United States Patent [19]

Ritscher et al.

[11] Patent Number: 5,084,590
[45] Date of Patent: Jan. 28, 1992

[54] TRIMETHOXYSILANE PREPARATION VIA THE METHANOL-SILICON REACTION USING A CONTINUOUS PROCESS AND MULTIPLE REACTORS

[75] Inventors: James S. Ritscher, Marietta; Thomas E. Childress, Newport, both of Ohio

[73] Assignee: Union Carbide Chemicals & Plastics Technology Corporation, Danbury, Conn.

[21] Appl. No.: 719,938

[22] Filed: Jun. 24, 1991

[51] Int. Cl.⁵ ............................................... C07F 7/18
[52] U.S. Cl. ................................................... 556/470
[58] Field of Search ........................................ 556/470

[56] References Cited

U.S. PATENT DOCUMENTS

| | | | |
|---|---|---|---|
| 2,389,931 | 11/1945 | Reed et al. | 556/470 X |
| 2,473,260 | 6/1946 | Rechew | 200/448.8 |
| 3,072,700 | 1/1963 | de Wit | 260/448.8 |
| 3,627,807 | 12/1971 | Bleh et al. | 556/470 |
| 3,775,457 | 11/1973 | Marsaka et al. | 260/448.8 R |
| 4,288,604 | 9/1981 | Magee et al. | 556/470 |
| 4,727,173 | 2/1988 | Mendicino | 556/470 |
| 4,761,492 | 8/1988 | Childress et al. | 556/482 |
| 4,762,939 | 8/1988 | Mendicino | 556/470 |
| 4,931,578 | 6/1990 | Ohta et al. | 556/470 |
| 4,999,446 | 3/1991 | Moody et al. | 556/470 |

FOREIGN PATENT DOCUMENTS 163529  7/1979  Japan .
11538  2/1980  Japan .

Primary Examiner—Paul F. Shaver
Attorney, Agent, or Firm—Bonnie L. Deppenbrock

[57] ABSTRACT

A continuous process for producing trimethoxysilane by reacting methanol and silicon metal in the presence of a copper catalyst, and optionally in an inert solvent, in a multiple reactor system containing at least three reactors by having methanol in substantially vapor form flow countercurrently to a stream containing the silicon metal.

25 Claims, 1 Drawing Sheet

TRIMETHOXYSILANE PREPARATION VIA THE METHANOL-SILICON REACTION USING A CONTINUOUS PROCESS AND MULTIPLE REACTORS

BACKGROUND OF THE INVENTION

1. Field of the Invention

The present invention relates to a process for converting silicon metal and methanol to trimethoxysilane (TMS) and in particular to a process which is continuous and which employs multiple reactors that are serially connected.

2. Prior Art

The reaction between silicon metal and alcohol to produce alkoxysilanes and silicates is well established. As early as 1949, U.S. Pat. No. 2,473,260 described a process for the preparation of methyl silicates from methanol and silicon-copper masses. Subsequently, U.S. Pat. No. 3,072,700 taught the preparation of alkoxysilanes from silicon metal and alcohol in a fluidized bed reactor.

A patent covering the production of trialkoxysilanes is U.S. Pat. No. 3,775,457. One of the problems associated with the process of the patent is the difficulty of removing the unreacted alcohol from the desired silane because of the formation of a trimethoxysilane/methanol azeotrope and the reaction of TMS with methanol to form tetramethoxysilane.

Several patents disclose solutions to the problem of azeotrope formation. For example, Japanese Laid Open Application No. 1980-11538 describes a process to produce trimethoxysilane wherein the unreacted methanol in the product is removed by breaking the trimethoxysilane-methanol azeotrope by adding a third component, e.g., hexane, in an amount proportional to the amount of methanol present and then distilling to remove the methanol as the hexane-methanol azeotrope. U.S. Pat. No. 4,761,492, discloses a process in which methanol is separated from crude product containing trimethoxysilane using extractive distillation with tetramethoxysilane as the solvent. U.S. Pat. No. 4,999,446 discloses a process for converting silicon metal and methanol to trimethoxysilane in which the trimethoxysilane/methanol azeotrope is recycled to a reactor without employing a separate azeotropic or extractive distillation step. In these patents, the direct reaction of methanol with silicon metal takes place as "a batch process", "batchwise" or "batchwise or semicontinuously".

The direct reaction is not carried out continuously in the above-mentioned patents because fines (particles of catalyst, impurities, and/or unreacted silicon metal) build up inside the reactor. In order to remove the fines from the reactor the reaction system must be shut down. Further, in the art, silicon metal has not been fed continuously because even greater amounts of fines would form. The presence of fines in the reactor results in one or more of the following problems. Fines can cause the slurry to foam. Also, fines can act as a catalyst for the reaction of TMS and methanol, thereby producing tetramethoxysilane (TTMS), an undesirable by-product, resulting in lower yield and less pure TMS. The presence of large amounts of fines also makes the recovery of solvent by filtration difficult.

Accordingly, a need exists for a commercially attractive process for producing trimethoxysilane that allows silicon metal to be fed continuously to the reactor system and that allows for the easy removal of fines.

SUMMARY OF THE INVENTION

The present invention provides a continuous process for producing trimethoxysilane in a serially connected multiple reactor system having at least three reactors and in which the reactors are each maintained at a temperature of at least 180° C. The process comprises:

(1) charging
  (i) silicon metal; and
  (ii) at least one catalyst to a first reactor;

(2) charging a solvent to a first reactor or a second reactor of the multiple reactor system to form a slurry;

(3) feeding a stream from the first reactor to an intermediate reactor;

(4) feeding a stream from an intermediate reactor to a final reactor;

(5) introducing methanol in substantially vapor form below the top level of the slurry in the final reactor such that the methanol flows countercurrently through the multiple reactor system and enters each reactor in the series below the top level of the slurry of each reactor;

(6) removing spent solvent and fines from the final reactor; and (7) removing a Product stream containing substantially trimethoxysilane from the first reactor. Optionally, the spent solvent is filtered and recycled to the first reactor and the fines are discarded. Preferably, three or four reactors are employed in the process of the present invention.

DETAILED DESCRIPTION OF THE DRAWING

Figure 1:
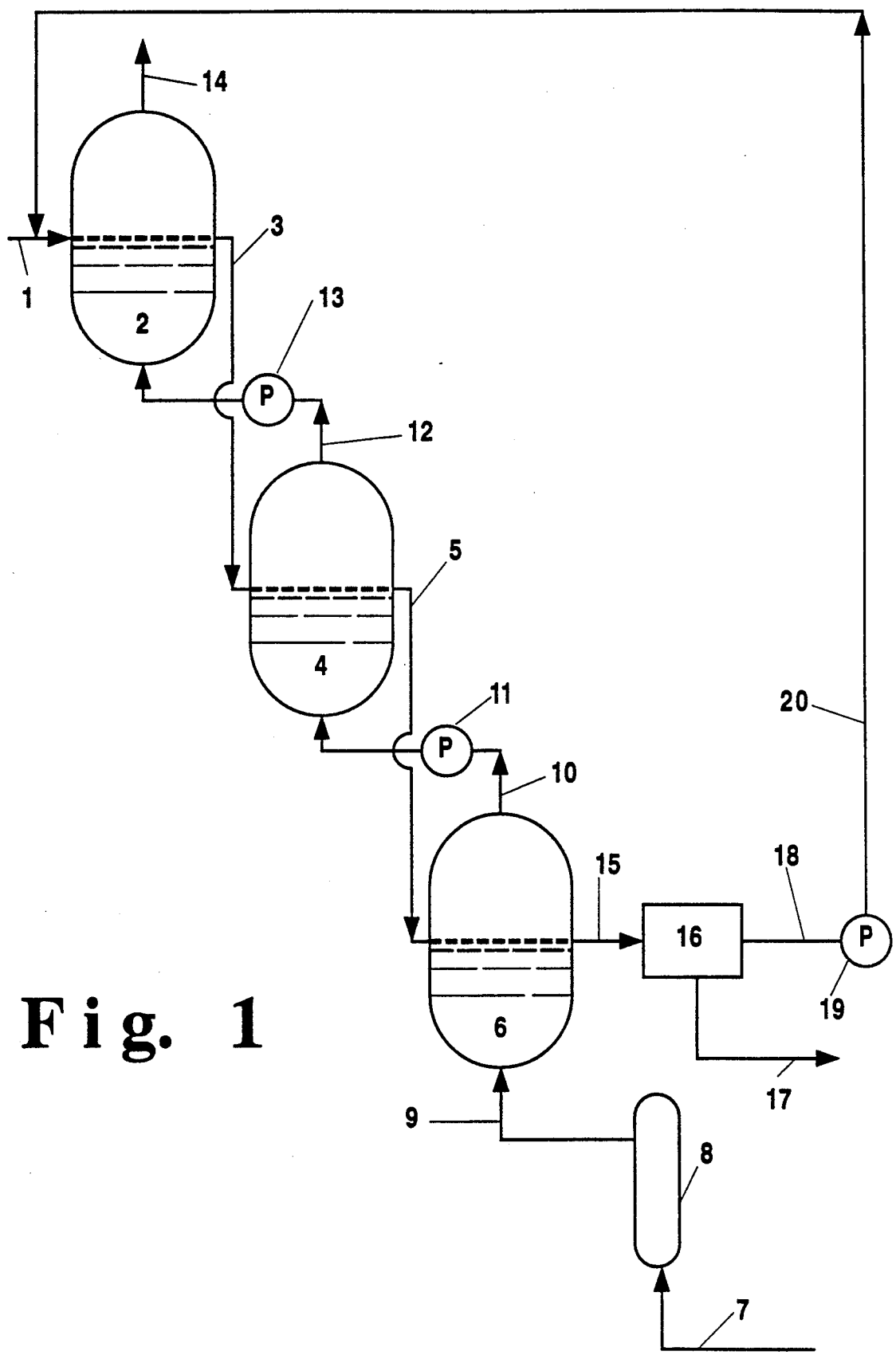
FIG. 1 illustrates schematically the stream flow and operational steps which can be employed in one embodiment of the process of the present invention.

Referring to FIG. 1, in a preferred embodiment of the invention, a feedstream (1) containing silicon metal, a catalyst, and a solvent is fed continuously to a first reactor (2). From the first reactor, a second stream (3) containing silicon metal and a catalyst along with a solvent flows by gravity and/or pumping means to an intermediate reactor (4) forming a slurry. From the intermediate reactor (4) a third stream (5) containing silicon metal, a catalyst, and solvent flows by gravity and/or pumping means to a final reactor (6) forming a slurry. Methanol (7) is introduced via a vaporizer (8) and fed as a gaseous stream (9) to the final reactor (6). The substantially vaporized methanol enters the final reactor below the top level of the slurry in the final reactor. From the final reactor (6) the vaporized methanol stream (10), now containing some trimethoxysilane formed by the reaction of the methanol with the silicon metal in reactor (6), is passed to a compressor (11) prior to being sent to the intermediate reactor (4). Again, the methanol/trimethoxysilane stream enters the intermediate reactor below the top level of the slurry contained in the intermediate reactor. From the intermediate reactor (4) the vaporous stream (12) containing TMS crude product and the remaining unreacted methanol is passed to another compressor (13) prior to being sent to the first reactor (2). The vaporous stream enters the first reactor below the top level of the slurry contained in the first reactor. Trimethoxysilane, containing less than about 2% of unreacted methanol, is removed from the first reactor via a crude product effluent stream (14). A slurry (15) containing fines or spent solids such as silicon metal, spent catalyst particles, and solvent is removed from the final reactor (6), and filtered (16). After filtering (16), the fines are discarded (17) and the solvent (18) is transferred via a pump (19) to the first reactor (2) via stream (20).

DETAILED DESCRIPTION OF THE INVENTION

The reaction by which trimethoxysilane is produced in the process of the present invention is illustrated by the following equation:

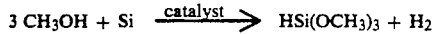

$$3\ CH_3OH + Si \xrightarrow{\text{catalyst}} HSi(OCH_3)_3 + H_2$$

In the process of the present invention, the methanol-silicon metal reaction is effected in multiple reactors that are serially connected. Any reactors in which silicon metal and catalyst can be contacted with methanol at a reaction temperature of at least 180° C. are suitable.

Two reactors in series can be employed to effect the process of the invention. However, when two reactors are employed, the stream containing the silicon metal and the stream containing the methanol must flow sufficiently slowly so that the silicon-methanol reaction can take place and to maintain high methanol conversion. Practically speaking, using only two reactors is too time consuming or slow for commercial consideration. Accordingly, the preferred number of reactors is three or four. Most preferably three reactors are used. It is to be understood, however, that as many as six or more reactors can be used. Generally, while more than six reactors can be used, using more than six is less desirable for economical considerations.

In the process of the present invention silicon metal, catalyst, and optionally a solvent are introduced to the first reactor in the series If solvent is not introduced into the first reactor of the series, it must be introduced into the second reactor, or next reactor, in the series. When no solvent is employed in the first reactor in the series, the first reactor can be, but is not limited to, a fluidized bed, fixed bed, or moving bed reactor (i.e., a two-phase, gas-solid contacting reactor). However, it is preferred to use a solvent in the first reactor as well as in all the other reactors employed in the process.

When solvent is employed in the first reactor, the first reactor and subsequent intermediate and final reactors which can be employed in the process of the invention are gas-liquid-solid contacting reactors such as, but not limited to, a slurry reactor (three-phase fluidized bed), a continuously stirred tank reactor, a mechanically agitated tank, and a trickle bed. Preferably, advanced gas reactors ("AGR") such as those described in U.S. Pat. Nos. 4,328,175 and 4,454,077 and available from Union Carbide Industrial Gases, Inc. or slurry reactors are employed.

The individual reactors employed in the series of multiple reactors of the invention can be of the same type or different types. For example, the first reactor in the series, if no solvent is present, can be a reactor selected from the group consisting of a fluidized bed reactor, moving bed reactor, or fixed bed reactor, and intermediate and final reactors can be reactors selected from the group consisting of a slurry reactor, a continuously stirred tank reactor, or advanced gas reactor. In the process of the present invention it is preferred that all of the reactors are gas-liquid-solid . contacting (or three phase) reactors selected from the group consisting of a slurry reactor, a continuously stirred tank reactor, or advanced gas reactor. In a most preferred embodiment of the invention all of the reactors are of the same type.

As used in this discussion, slurry refers to the reactants contained in a reactor, and stream refers to the reactants as they flow between reactors in the series.

During start-up, methanol is introduced into the slurry of the final reactor at a fixed rate. The methanol so introduced flows through each reactor in the series in turn and countercurrently to the flow of the stream containing the other reactants. The methanol may be in liquid or vapor form. Preferably, the methanol is vaporized. The methanol enters into each reactor at a point below the top level of the slurry in that reactor. Preferably, the vaporized methanol enters at or near the bottom of each reactor. The methanol is caused to flow countercurrently either by the autogenous pressure of the reaction system through maintaining heat and/or by use of compressors on line in the streams. If autogenous pressure is relied on to cause the methanol to flow countercurrently, gravity alone cannot be used to cause the streams to flow. In such case, pumps are employed to cause the streams to flow. If compressors are used to cause the methanol to flow countercurrently, then gravity may be applied to the streams. However, it is preferred in the practice of the present invention to use a combination of gravity, pumps, and compressors.

The reaction typically displays a one or two hour induction period. After the initial induction period, the rate of the methanol feed is adjusted such that steady-state conversion of at least 98% and preferably 99% of the methanol is achieved. Thereafter, "fresh" methanol in substantially vaporized form is introduced into the final reactor of the series until such time as the reactors are shut down, such as for maintenance.

In continuous operation, "make-up" silicon metal, catalyst, and solvent are fed to the first reactor of the series at a rate such that the amount of silicon metal in the first reactor remains constant or substantially constant. During operation, the stream flows from one reactor to another by means of gravity, pumping means, or by a combination of the two. When gravity is utilized to cause the stream to flow, the reactors are positioned or elevated such that each reactor is higher than the next reactor in the series. Preferably, a combination of gravitational and pumping means are employed.

Exhausted or "spent" solvent containing fines (primarily silicon metal) and/or other impurities, such as spent catalyst, is removed from the final reactor at a rate such that, at steady state, less than about ten percent of the initial silicon metal charged to the first reactor remains. During start-up the initial amount of silicon metal in the final reactor will be removed at a rate higher than that which corresponds to 90% silicon consumption, eventually the rate of removal will drop to the desired level, and metal wastage will cease. That is, the silicon metal is consumed on average to about 90% or other value based on economic considerations. One skilled in the art will recognize that by varying the rate of pumping and the rate of fresh methanol introduction, the overall conversion of silicon metal and methanol can be varied to obtain a desired level of silicon conversion and/or methanol conversion. In the most preferred embodiment in which three advanced gas reactors are used in series, the preferred methanol conversion per reactor is about 85%. That is, the proportion of methanol entering each reactor is on average converted to product to the extent of about 85%. One skilled in the art will recognize that the rate of methanol introduction is varied empirically until the desired overall conversion is achieved.

The exhausted solvent and fines from the final reactor is filtered by means well-known to those skilled in the art to remove spent catalyst, silicon metal or other impurities. The filtered solvent may then be optionally further treated to remove impurities, if any, and may then be recycled to the first reactor or to the second reactor in the series, if no solvent was employed in the first reactor in the series.

Silicon

The silicon metal used in the process of this invention can generally be any commercially available grade of silicon in particulate form. A typical composition of commercial silicon metal useful in this invention, expressed in percent by weight, is silicon-98.5%; iron-less than 0.50%; aluminum-0.20 to 0.35%; lead-less than 10 ppm; boron-less than 20 ppm. Generally smaller particle size (less than about 420 microns) is preferred for ease of processing. Most preferably the particle size ranges from about 75 to 300 microns. Sieving of ground silicon to regulate particle size is optional. Silicon metal and an effective amount of catalyst can be added continuously to any or all of the serially connected reactors during the process of the present invention. Preferably, the silicon metal along with catalyst is added to the first reactor of the series, and the silicon metal and catalyst flow by means of gravity and/or pumping means from one reactor to the next reactor in the series.

The presence of tin in the reaction of the process of the present invention has adverse effects on the reaction rate and so whenever possible should be avoided (e.g., amounts as low as 75 parts per million have been shown to have an adverse effect on the reaction).

Methanol

Methanol is employed in at least a stoichiometric amount based on the amount of silicon metal used. Methanol may be introduced into the reaction as a gas or a liquid. However, it is preferred to introduce methanol as a gas or in substantially vaporized form. Methanol is introduced into the final reactor of the process of the invention such that the methanol moves or flows countercurrently to the streams containing the silicon metal and other components such as catalyst and solvent. The methanol moves or flows countercurrently through the serially connected reactors due to the autogenous pressure of the system or by means of compressors in the methanol-product stream.

Other alcohols, such as ethanol, will react to produce the corresponding trialkoxysilane in the Process of the invention. However, since such reactions do not require high conversion rates and separations are readily accomplished by simple distillations, other processes known to the art are more feasible and advantageous.

Catalyst

The catalyst used in the process of this invention is present in each of the serially connected reactors in an amount effective to catalyze the reaction of the methanol and silicon metal to form trimethoxysilane. Generally an effective amount ranges from about 0.01 to about 5 parts by weight of catalyst per 100 parts by weight of the silicon metal. Usually the amount of catalyst will be from about 0.1 to about 2.6 parts by weight per 100 parts by weight of the silicon metal. The preferred amount of catalyst is from about 0.1 to about 0.7 parts by weight per 100 parts by weight of silicon metal.

In general, the catalyst is introduced in the first reactor and flows to each reactor in turn along with the silicon metal and solvent. Under certain conditions, such as when higher conversion is desired in the intermediate reactor(s) and/or final reactor, additional catalyst can be added to such reactor(s) separately.

The preferred catalysts employed in the process of the present invention are selected from the group consisting of powdered metallic copper, any anhydrous copper compounds, and mixtures thereof.

Examples of anhydrous copper compounds particularly suitable for use alone or in mixtures are the copper oxides, e.g. cupric oxide and cuprous oxide; copper halides, e.g. cupric chloride, cuprous chloride, cuprous bromide, cupric bromide; copper nitrates; copper salts of lower aliphatic acids such as cupric formate and cupric acetate; copper carbonates; copper hydroxides; copper cyanides; intermetallic copper compounds such as lead-free bronzes and brasses; and copper acetylacetonate. This, however, is not a restrictive or exclusive list. Preferred catalysts include cupric oxide, cuprous oxide, cupric chloride, copper hydroxides and their mixtures. Most preferably, stabilized copper (II) hydroxide is employed. Stabilized copper hydroxide is available from Alfa Products, Don Ingram Company, Inc., and Kocide Chemical Corporation.

Copper compounds specifically to be avoided as catalysts in the present process are those such as copper phosphide, copper sulfides and inter-metallic compounds of lead and copper.

Metallic silver, its compounds such as silver oxide and silver chloride, and their mixtures are also known to be effective catalysts but are not considered optimum for the present process.

Solvent

In the process of the present invention a solvent is used in at least one reactor, to disperse the silicon in a fluid state (slurry). In the preferred embodiment of the present invention a solvent is utilized in all the reactors in the series. Solvents useful in the process of the present invention are inert, that is, a solvent that does not substantially (or significantly) degrade under the reaction conditions of the process. Generally, the inert solvent employed in the present invention is a high-temperature stable organic solvent. Suitable inert solvents that may be employed include paraffinic hydrocarbons (e.g., dodecane); polyalkylated aromatic hydrocarbons (e.g. THERMINOL TM 59, THERMINOL TM 60, THERMINOL TM 66,); and mixtures thereof. Polyalkylated aromatic hydrocarbons and mixtures thereof are the preferred solvents for use in the present invention. The most preferred solvent is THERMINOL TM 59. THERMINOL TM is the Monsanto Company tradename for heat transfer fluids having thermal stability and low vapor pressure, i.e., not higher than about 170 Torr at 250° C.

The amount of solvent employed in each reactor is a function of the amount of silicon metal present. Generally, from one part of solvent per two parts of silicon metal (1:2) to four parts of solvent per one part of silicon metal (4:1) will be required. Preferably this ratio ranges from 1:1 to 2:1.

Reaction Conditions

The reaction effected in each reactor is generally conducted at temperatures above about 180° C. but below such a temperature that would degrade or decompose the reactants or solvents. Preferably the reaction temperature in each reactor is maintained in a range from about 200° C. to about 280° C. Most Preferably the reaction temperature in each reactor is about 220° C. to 260° C. The reaction could of course be run at higher temperatures although at no particular advantage. The pressure at which the reaction of the present process is conducted in each reactor is not critical and may be varied from 0.1 to 10 atmospheres, preferably 1 to 2 atmospheres. It is most preferred to operate each reactor at atmospheric pressure.

Preferably the contents of the reaction mixture are agitated to maintain a well mixed slurry of the silicon metal particles and methanol in the solvent in each reactor.

Whereas, the exact scope of the instant invention is set forth in the appended claims, the following specific example illustrates certain aspects of the present invention. However, the example is set forth for illustration only and is not to be construed as limiting on the present invention. All parts and percentages are by weight unless otherwise specified.

EXAMPLE

A feedstream containing 1 part silicon metal, 0.01 part catalyst, and 2 parts solvent is fed continuously to a first reactor that is agitated and heated to about 250° C. From the first reactor the slurry stream flows via gravity and is pumped to a second reactor in the series that is also agitated and heated to about 250° C. From the second (intermediate) reactor, the slurry stream flows via gravity and is pumped to a third reactor in the series that is also agitated and heated to about 250° C. Methanol is vaporized in a vaporizer and is introduced into the third (final) reactor at a point at or near the bottom of the reactor below the top level of the slurry contained in the third reactor. From the third reactor the vaporized methanol stream containing some TMS and by-products is passed through a compressor and enters the second reactor at a point at or near the bottom of the second reactor, below the surface of the slurry contained in the second reactor. This vaporized stream containing methanol and crude product leaves the second reactor, passes through another compressor and enters the first reactor at or near the bottom of the first reactor, again below the top level of the slurry in the reactor. A product stream containing substantially TMS is removed from or near the top of the first reactor. Spent solvent and fines are removed from the third reactor and filtered. The filtered solvent is recycled to the first or the second reactor in the series. When a steady state is obtained, the methanol conversion of the reactor system overall is maintained at about 99%. Also, when a steady state is obtained, the silicon conversion of the reactor system overall maintained is about 90% with product selectivity (TMS/TTMS) being about 10 to 1.

We claim:

1. A continuous process for producing trimethoxysilane in a serially connected multiple reactor system having at least three reactors and in which the reactors are each maintained at a temperature of at least 180° C., which process comprises:
   (1). charging
      (i) silicon metal, and
      (ii) at least one catalyst to a first reactor;
   (2) charging a solvent to a first reactor or to a second reactor of the multiple reactor system to form a slurry;
   (3) feeding a stream comprising silicon metal, a catalyst, and optionally a solvent from the first reactor to an intermediate reactor;
   (4) feeding a stream comprising silicon metal, a catalyst, and a solvent from the intermediate reactor to a final reactor;
   (5) introducing methanol in substantially vapor form below the top level of the slurry in the final reactor such that the methanol flows countercurrently through the multiple reactor system and enters each reactor in the series below the top level of the slurry of each reactor;
   (6) removing spent solvent and fines from the final reactor; and
   (7) removing a product stream containing substantially trimethoxysilane from the first reactor.

2. A process according to claim 1 wherein the multiple reactor system contains three reactors.

3. A process according to claim 1 wherein the multiple reactor system contains three to six reactors.

4. A process according to claim 1/wherein the temperature ranges from about 200° C. to 280° C.

5. A process according to claim 1 wherein the temperature ranges from about 220° C. to 260° C.

6. A process according to claim 1 wherein solvent is charged to the first reactor.

7. A process according to claim 1 wherein solvent is charged to a second reactor in the series.

8. A process according to claim 1 wherein all the reactors of the multiple reactor system contain at least one inert solvent.

9. A process according to claim 8 wherein the solvent is selected from the group consisting of paraffinic hydrocarbon, polyalkylated aromatic hydrocarbon and mixtures thereof.

10. A process according to claim 9 wherein the solvent is a polyalkylated aromatic hydrocarbon.

11. A process according to claim 1 wherein the silicon metal is in particulate form.

12. A process according to claim 1 wherein the catalyst is a copper catalyst selected from the group consisting of cupric oxide, cuprous oxide, cupric chloride, cuprous chloride, copper hydroxide and mixtures thereof.

13. A process according to claim 12 wherein the catalyst is copper hydroxide.

14. A process according to claim 13 wherein the catalyst is stabilized copper (II) hydroxide.

15. A process according to claim 12 wherein the effective amount of copper catalyst per reactor ranges from about 0.1 to about 2.6 parts by weight per 100 parts by weight of silicon metal.

16. A process according to claim 15 wherein the effective amount of copper catalyst per reactor ranges from about 0.1 to 0.7 parts by weight per 100 parts by weight of silicon metal.

17. A process according to claim 8 wherein the solvent is present in an amount ranging from one part of solvent per two parts of silicon metal (1:2) to four parts of solvent per one part of silicon metal (4:1).

18. A process according to claim 17 wherein the solvent is present in an amount ranging from 1:1 to 1:2 parts of solvent to silicon.

19. A process according to claim 1 wherein the percent methanol conversion of the reactor system is maintained at about 85% per reactor.

20. A process according to claim 1 wherein each reactor is operated at atmospheric pressure.

21. A process according to claim 1 wherein the first reactor is selected from the group consisting of a fluidized bed reactor, a moving bed reactor, a slurry reactor, a mechanically agitated tank, and a trickle bed.

22. A process according to claim 1 wherein the reactors are selected from the group consisting of a slurry reactor, a mechanically agitated tank, and a trickle bed.

23. A process according to claim 1 wherein the reactors are advanced gas reactors.

24. A process according to claim 1 wherein fines are separated from spent solvent by filtration.

25. A process according to claim 24 wherein the spent solvent is recycled to the first reactor or to the second after the filtration step.

* * * * *